United States Patent
Popp et al.

(10) Patent No.: US 6,915,829 B2
(45) Date of Patent: Jul. 12, 2005

(54) APPARATUS AND METHOD FOR CUTTING AND PLACING LIMP PIECES OF MATERIAL

(75) Inventors: Robert L. Popp, Hortonville, WI (US); Joseph D. Coenen, Kaukauna, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 372 days.

(21) Appl. No.: 10/195,246

(22) Filed: Jul. 15, 2002

(65) Prior Publication Data

US 2004/0007318 A1 Jan. 15, 2004

(51) Int. Cl.$^7$ .............................................. B32B 31/00
(52) U.S. Cl. ..................... 156/519; 156/263; 156/301; 156/303; 156/265
(58) Field of Search ................................ 156/265, 519, 156/259, 263, 264, 299, 300, 301, 302, 303, 511, 512, 521

(56) References Cited

U.S. PATENT DOCUMENTS

| | | | |
|---|---|---|---|
| 3,172,321 A | 3/1965 | Schrader | |
| 3,311,032 A | 3/1967 | Lucas | |
| 3,557,648 A | 1/1971 | Coffin et al. | |
| 3,772,120 A | 11/1973 | Radzins | |
| 3,860,002 A | 1/1975 | Kolbach | |
| 3,878,771 A | * 4/1975 | Malcolm | 493/67 |
| 4,010,763 A | 3/1977 | Dreher | |
| 4,233,331 A | * 11/1980 | Lemke et al. | 426/407 |
| 4,364,787 A | 12/1982 | Radzins | |
| 4,397,410 A | 8/1983 | Schueler | |
| 4,485,710 A | 12/1984 | Schlisio et al. | |
| 4,525,229 A | 6/1985 | Suzuki et al. | |
| 4,543,141 A | 9/1985 | Bradley et al. | |
| 4,663,220 A | 5/1987 | Wisneski et al. | |
| 4,704,116 A | 11/1987 | Enloe | |
| 4,925,520 A | 5/1990 | Beaudoin et al. | |

(Continued)

FOREIGN PATENT DOCUMENTS

| | | |
|---|---|---|
| EP | 0 217 032 | 4/1987 |
| EP | 1 132 325 A2 | 9/2001 |
| WO | WO 00/37009 | 6/2000 |

OTHER PUBLICATIONS

International Search Report, PCT/US 03/10104, 2 pages, Jul. 18, 2003.

*Primary Examiner*—Linda Gray
(74) *Attorney, Agent, or Firm*—Senniger Powers

(57) ABSTRACT

Apparatus and method for cutting and placing limp pieces of material on an article component. The apparatus, which is particularly constructed for positioning the relative placement of two cut piece, includes a vacuum conveyor which holds the article component in a regular and secure position prior to and during placement of a cut piece onto the component. A cut piece is formed and transferred to a conveyor on a single, constant speed anvil roll without the need for intervening rolls.

26 Claims, 10 Drawing Sheets

U.S. PATENT DOCUMENTS

| | | |
|---|---|---|
| 4,940,464 A | 7/1990 | Van Gompel et al. |
| 5,046,272 A | 9/1991 | Vogt et al. |
| 5,104,116 A | 4/1992 | Pohjola |
| 5,109,741 A | 5/1992 | Fuchs |
| 5,110,403 A | 5/1992 | Ehlert |
| 5,172,621 A | 12/1992 | Minarelli et al. |
| 5,200,020 A | 4/1993 | Collins et al. |
| 5,224,405 A | 7/1993 | Pohjola |
| 5,226,344 A | 7/1993 | Rosemann |
| 5,226,992 A | 7/1993 | Morman |
| 5,236,539 A | 8/1993 | Rogberg et al. |
| 5,249,493 A | 10/1993 | Breton |
| 5,253,561 A | 10/1993 | Wynn |
| 5,261,996 A | 11/1993 | Rossini |
| 5,407,513 A | 4/1995 | Hayden et al. |
| 5,415,716 A | 5/1995 | Kendall |
| 5,591,297 A | 1/1997 | Ahr |
| 5,659,538 A | 8/1997 | Stuebe et al. |
| 5,695,105 A | 12/1997 | Ohara |
| 5,746,869 A | 5/1998 | Hayden et al. |
| 5,766,389 A | 6/1998 | Brandon et al. |
| 5,776,289 A | 7/1998 | Steidinger |
| 6,029,552 A | 2/2000 | Harris |
| 6,074,333 A | 6/2000 | Rajala et al. |
| 6,149,755 A | 11/2000 | McNichols et al. |
| 6,165,306 A | 12/2000 | Rajala |
| 6,227,541 B1 | 5/2001 | Couillard et al. |
| 6,319,347 B1 | 11/2001 | Rajala et al. |
| 6,544,375 B1 | 4/2003 | Schmitz |

\* cited by examiner

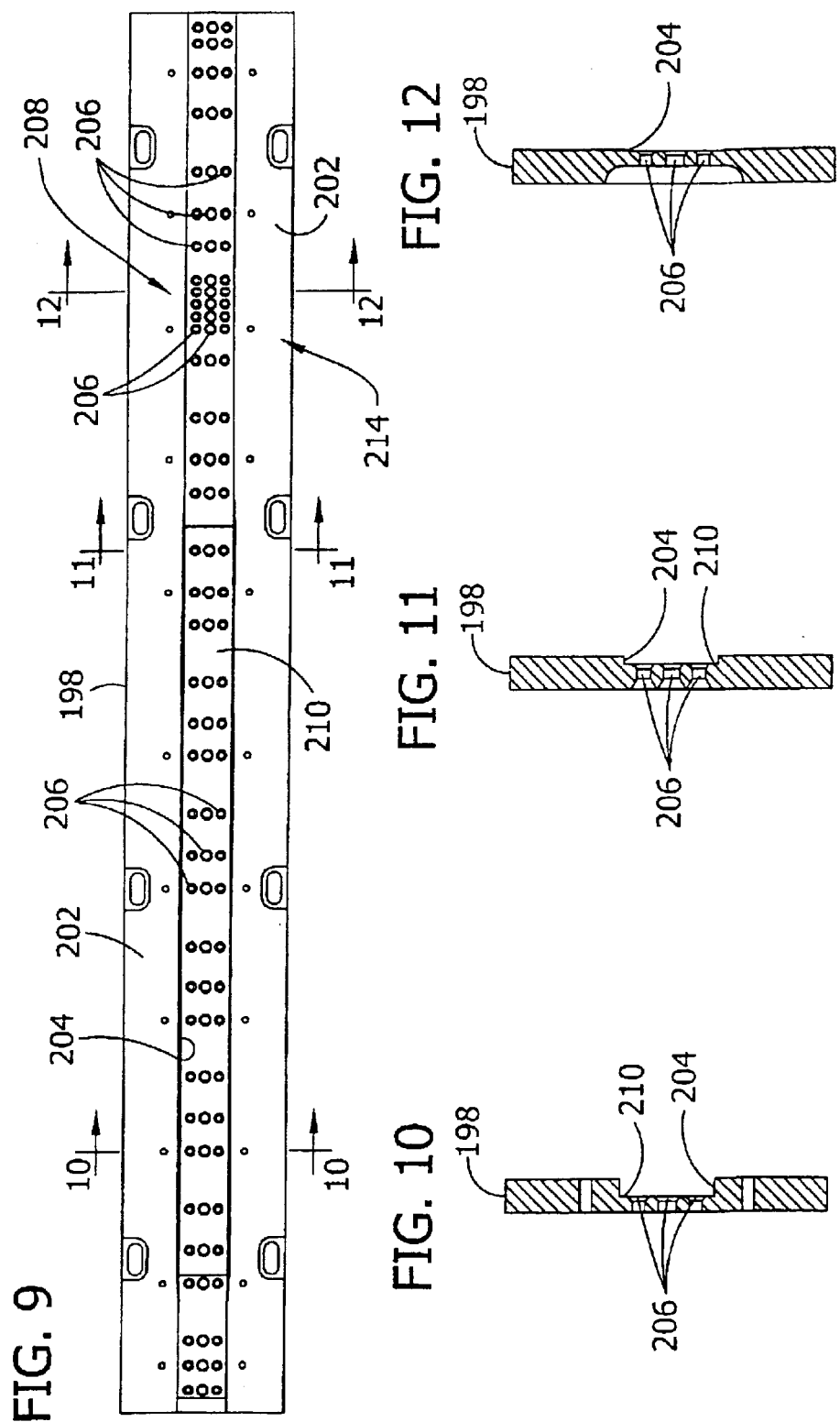

APPARATUS AND METHOD FOR CUTTING AND PLACING LIMP PIECES OF MATERIAL

BACKGROUND OF THE INVENTION

The present invention relates generally to apparatus and methods for making articles composed of multiple pieces of limp material, and more particularly to apparatus and methods for precise location of a cut piece onto a discontinuous component of an article.

Garments, and more particularly disposable absorbent garments, have numerous applications including diapers, training pants, feminine care products, and adult incontinence products. A typical disposable absorbent garment is formed as a composite structure including an absorbent assembly disposed between a liquid permeable bodyside liner and a liquid impermeable outer cover. These components can be combined with other materials and features such as elastic materials and containment structures to form a product which is specifically suited to its intended purposes. A number of such garments include fastening components which are intended to be secured together (e.g., pre-fastened) during manufacture of the garment so that the product is packaged in it's fully assembled form.

For example, one such pre-fastened garment is a child's training pants, which have a central absorbent chassis and front and back side panels extending laterally out from the chassis adjacent longitudinally opposite ends thereof. Each of the front and back side panels has a fastening component thereon, such as a hook or a loop fastener. Conventionally, these components are cut from a roll of hook (and loop) material and placed onto a continuous web. The material to be cut extends from the roll into engagement with an anvil roll. The material slides on the roll, which is turning at a speed greater than the speed at which the material fed to the roll. A die or knife roll periodically engages the material on the anvil roll to sever a piece from the material, and the piece is then carried by the anvil roll to another roll or directly to the web of material where the cut piece is placed on the web. It is known to apply a vacuum to the anvil roll for the purpose of holding the cut piece on the roll while it is being transported.

A difficulty associated with this type of cut and place operation is control of the cut piece of material while on the anvil roll. Material such as hook material or loop material can be long and thin. It is difficult to control the material on the anvil. The material tends to move from side to side as it slides on the roll. Thus, the accuracy of the placement of the cut piece onto the other component is compromised. Controlling the position of the material is desirably not achieved by the addition of structure which will make it more difficult ultimately to release the cut piece onto the other component.

SUMMARY OF THE INVENTION

The present invention is particularly useful in positioning a first cut piece of material onto another surface, such as a second cut piece of material which is discontinuous. The apparatus positively controls the orientation and position of the second cut piece of material as it approaches a transfer point where it receives the first cut piece of material. In one embodiment, the first cut piece is applied directly from the anvil roll on which it is cut to a vacuum conveyor. A web of material from which the first cut piece is severed is retained in a groove on an anvil roll prior to cutting the first cut piece from the web for increased accuracy in placement of the first cut piece on the second cut piece.

In one aspect of the present invention, apparatus for cutting and placing first cut pieces of material onto second pieces of material generally comprises a vacuum conveyor including a support adapted to support said second pieces of material and to hold said second pieces in place on the support. An anvil roll includes a wheel mounted in generally opposed relation with the movable support of the vacuum conveyor to define a transfer nip. The wheel is adapted for rotation about an axis of rotation and for receiving an end segment of a web of said first material thereon. A cutter roll mounted for rotation about an axis generally parallel to the axis of rotation of the wheel includes a knife periodically engageable with said first material web end segment when the end segment is on the wheel for severing the first cut pieces of material from the web of first material. The wheel is adapted to retain said first cut pieces thereon and to carry said first cut pieces to the movable support of the vacuum conveyor for placement of said first cut pieces on said second pieces.

In another aspect of the present invention, an apparatus cuts and places fastening components on pairs of side panels located on opposite sides of an assemblage in the manufacture of absorbent garments, the pairs of side panels being spaced apart in a machine direction. The apparatus generally comprises a vacuum conveyor comprising a continuous belt and rollers mounted for movement of the continuous belt in a circuit. The continuous belt is adapted to support the assemblage on an upper reach thereof, and to locate the side panels on the upper reach as the assemblage is moved by the conveyor belt. A vacuum plenum located under an upper reach of the conveyor belt supplies a vacuum pressure adjacent to the upper reach and the conveyor belt is porous for communicating the vacuum pressure through the belt to the side panels. An anvil roll includes two wheels mounted in generally opposed relation with the conveyor belt to define transfer nips. The wheels are adapted for rotation about an axis of rotation, with each wheel being adapted to receive an end segment of a respective web of fastening component material thereon. A cutter roll mounted for rotation about an axis generally parallel to the axis of rotation of the wheel includes a knife periodically engageable with the fastening component material end segment on each wheel when the end segment is on the wheel for severing the fastening components from the web of fastening component material. The wheels are adapted to retain the fastening components thereon and to carry the fastening components to the upper reach of the conveyor belt for placement of the fastening components onto respective side panels.

In still another aspect of the present invention, a method of cutting and placing first cut pieces of material on second pieces of material in a continuous process comprises cutting the second pieces from a web of second material and depositing the second pieces on a conveyor where they are restrained in position. The first cut pieces are cut from a web of first material engaging an anvil roll and transported on the anvil roll to a transfer point at the conveyor where the first cut pieces are transferred to the second pieces on the conveyor at the transfer point.

In a further aspect of the present invention, a method of applying fastening components to an assemblage in the manufacture of disposable pants generally comprises cutting side panels for the disposable pants from a web of side panel material and attaching the cut side panels to the assemblage at spaced apart locations along the length of the assemblage. The orientation and configuration of the side panels is controlled on a conveyor transporting the assemblage including the attached side panels. Fastening components are cut from a web of fastening component material on an anvil roll adjacent to the conveyor and transported to the anvil roll to a transfer point between the anvil roll and conveyor. The cut fastening components are transferred at the transfer point from the anvil roll to the side panels controlled by the conveyor.

Other aspects and features of the present invention will be in part apparent and in part pointed out hereinafter.

DEFINITIONS

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, while fibers having contact angles greater than 90 degrees are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning. The longitudinal axis lies in the plane of the garment and is generally parallel to a vertical plane that bisects a standing wearer into left and right body halves when the article is worn. The transverse axis lies in the plane of the article generally perpendicular to the longitudinal axis. The garment as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

BRIEF DESCRIPTION OF THE DRAWINGS

FIG. 9 is a flat lay out of a shell of an anvil roll of the fastener application station;

FIG. 10 is a section taken in the plane including line 10—10 of FIG. 9;

FIG. 11 is a section taken in the plane including line 11—11 of FIG. 9;

FIG. 12 is a section taken in the plane including line 12—12 of FIG. 9; and

Corresponding reference characters indicated corresponding parts throughout the several views of the drawings.

DETAILED DESCRIPTION OF THE DRAWINGS

The methods and apparatus of the present invention can be used to make a variety of garments. Examples of such garments include disposable absorbent articles such as diapers, training pants, feminine hygiene products, incontinence products, other personal care or health care garments, swim pants, athletic clothing, pants and shorts, and the like. For ease of explanation, the methods and apparatus of the present invention are hereafter described in connection with making child's training pants, generally indicated as 20 in FIG. 1. In particular, the methods and apparatus will be described in terms of those for making disposable training pants as described in U.S. patent application Ser. No. 09/444,083 titled "Absorbent Articles With Refastenable Side Seams" and filed Nov. 22, 1999 (corresponding to PCT application WO 00/37009 published Jun. 29, 2000) by A. L. Fletcher et al., the disclosure of which is incorporated herein by reference. Training pants 20 can also be constructed using the methods and apparatus disclosed in U.S. Pat. No. 4,940,464 issued Jul. 10, 1990 to Van Gompel et al.; and U.S. Pat. No. 5,766,389 issued Jun. 16, 1998 to Brandon et al.; the disclosures of which are also incorporated herein by reference.

Figure 1:
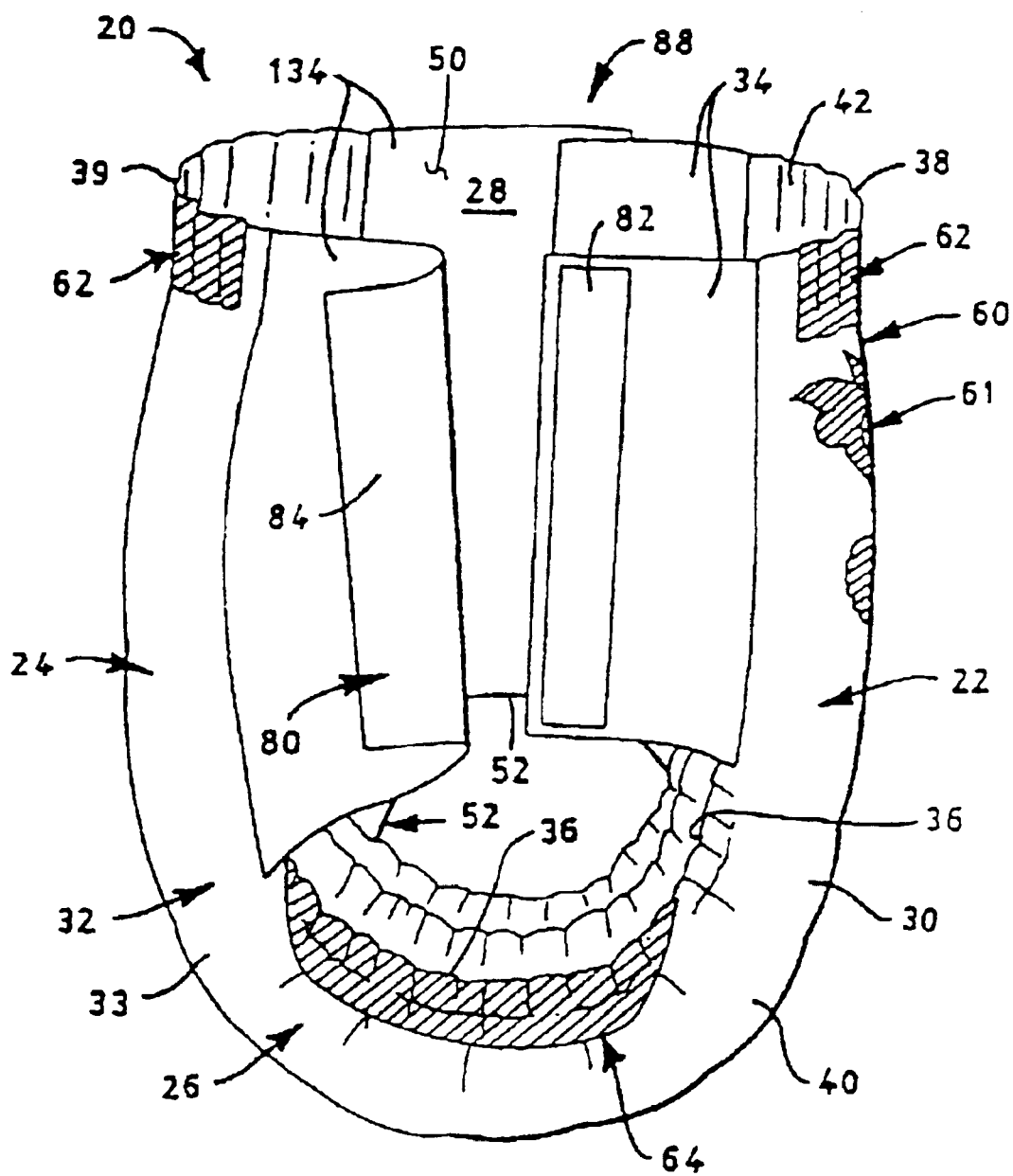
FIG. 1 is a side elevation of a child's training pants with a fastening system of the training pants shown engaged on one side of the training pants and disconnected on the other side of the training pants.

With reference now to the drawings, and in particular to FIG. 1, the training pants 20 are illustrated in a partially fastened condition and comprise an absorbent chassis 32 and a fastening system 80. The absorbent chassis 32 has a front waist region 22, a back waist region 24, a crotch region 26 interconnecting the front and back waist regions, an inner surface 28 which is configured to contact the wearer, and an outer surface 30 opposite the inner surface and configured to contact the wearer's clothing. With additional reference to FIGS. 2 and 3, the absorbent chassis 32 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 2:
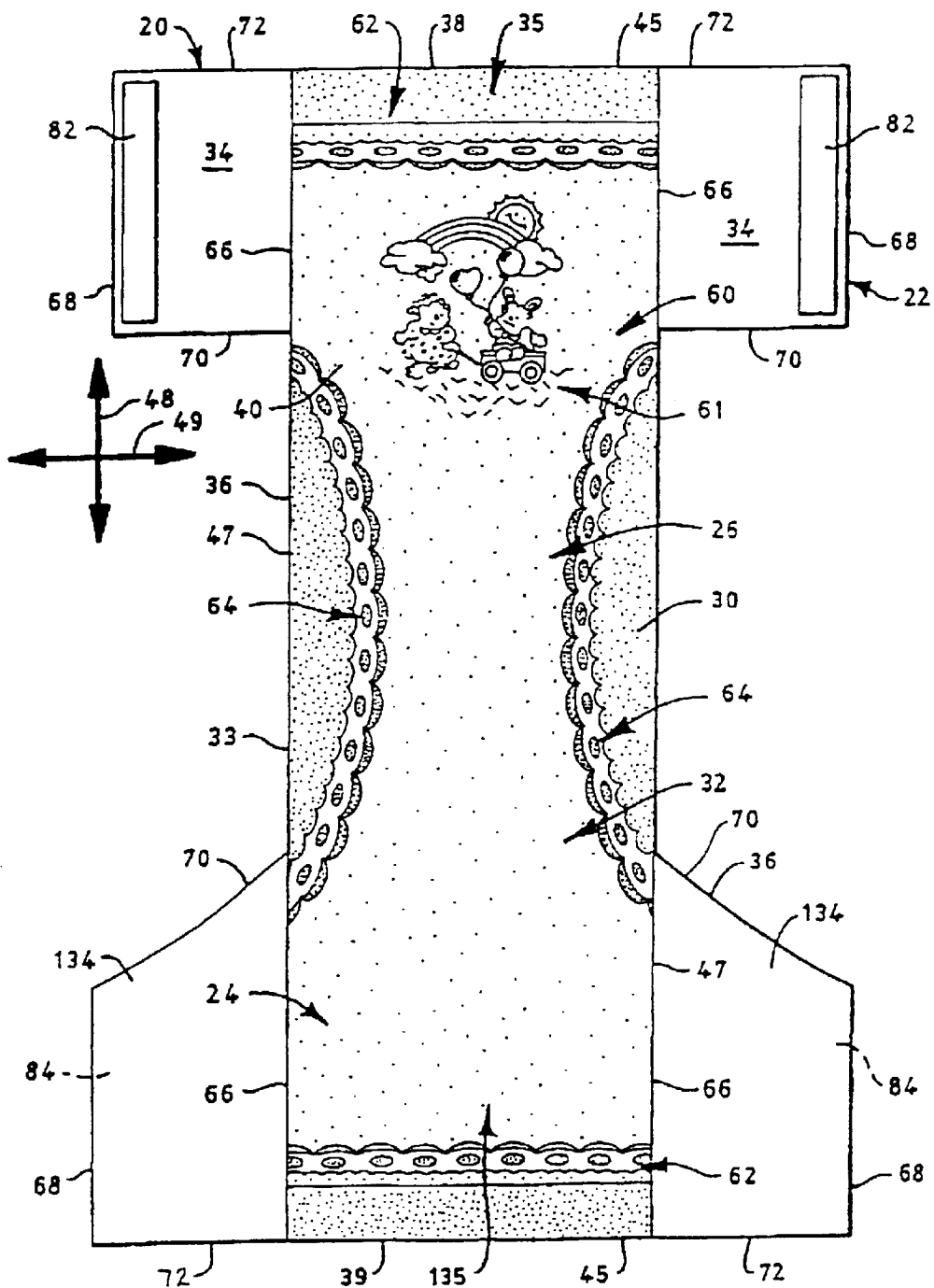
FIG. 2 is a bottom plan view of the training pants of FIG. 1 in an unfastened, stretched and laid flat condition to show the surface of the training pants which faces away from the wearer.
Figure 3:
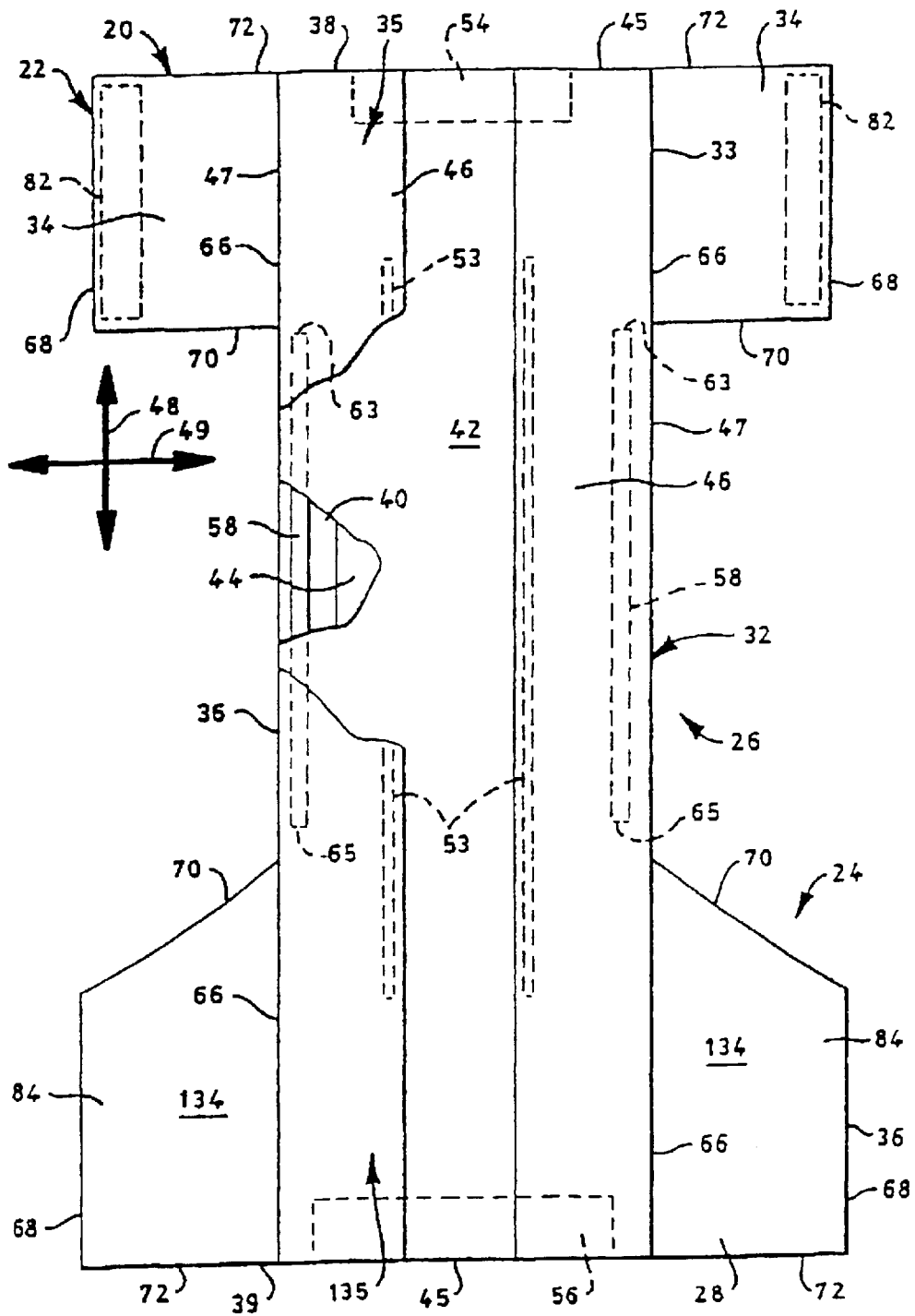
FIG. 3 is a top plan view of the training pants it its unfastened, stretched and laid flat condition to show the surface of the training pants which faces the wearer when the training pant is worn, with portions of the training pants being cut away to reveal underlying features.

The illustrated absorbent chassis 32 comprises a composite structure 33, which when laid flat is rectangular (but may have other shapes), and has a pair of laterally opposite front side panels 34 and a pair of laterally opposite back side panels 134 extending outward therefrom. The composite structure 33 and side panels 34 and 134 may comprise two or more separate elements, as shown in FIG. 1, or be integrally formed. Integrally formed side panels 34, 134 and composite structure 33 would comprise at least some common materials, such as the bodyside liner, flap composite, outer cover, other materials and/or combinations thereof, and/or could define a one-piece elastic, stretchable, or non-stretchable pants. The illustrated composite structure 33 comprises an outer cover 40, a bodyside liner 42 (FIGS. 1 and 3) which is connected to the outer cover in a superposed relation, an absorbent assembly 44 (FIG. 3) which is located between the outer cover and the bodyside liner, and a pair of containment flaps 46 (FIG. 3). The illustrated composite structure 33 has opposite ends 45 which form portions of the front and back waist edges 38 and 39, and opposite side edges 47 which form portions of the side edges 36 of the absorbent chassis 32 (FIGS. 2 and 3). For reference, arrows 48 and 49 depict the orientation of the longitudinal axis and the transverse or lateral axis, respectively, of the training pants 20.

With the training pants 20 in the fastened position as partially illustrated in FIG. 1, the front and back side panels 34, 134 are secured together to define a three-dimensional pants configuration having a waist opening 50 and a pair of leg openings 52. The front waist region 22 comprises the portion of the training pants 20 which, when worn, is positioned on the front of the wearer while the back waist region 24 comprises the portion of the training pants which, when worn, is positioned on the back of the wearer. The crotch region 26 of the training pants 20 comprises the portion of the training pants 20 which, when worn, is positioned between the legs of the wearer and covers the lower torso of the wearer. The front and back side panels 34 and 134 comprise the portions of the training pants 20 which, when worn, are positioned on the hips of the wearer. The waist edges 38 and 39 of the absorbent chassis 32 are configured to encircle the waist of the wearer when worn and together define the waist opening 50 (FIG. 1). Portions of the side edges 36 in the crotch region 26 generally define the leg openings 52.

The absorbent chassis 32 is configured to contain and/or absorb any exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 3) can be operatively joined with each containment flap 46 in any suitable manner as is well known in the art. The elasticized containment flaps 46 define an unattached edge which assumes an upright configuration in at least the crotch region 26 of the training pants 20 to form a seal against the wearer's body. The containment flaps 46 can be located along the side edges 36 of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 desirably although not necessarily include a front waist elastic member 54, a rear waist elastic member 56, and leg elastic members 58, as are known to those skilled in the art (FIG. 3). The waist elastic members 54 and 56 can be operatively joined to the outer cover 40 and/or the bodyside liner 42 along the opposite waist edges 38 and 39, and can extend over part or all of the waist edges. The leg elastic members 58 can be operatively joined to the outer cover 40 and/or the bodyside liner 42 along the opposite side edges 36 and positioned in the crotch region 26 of the training pants 20. The leg elastic members 58 can be longitudinally aligned along each side edge 47 of the composite structure 33. Each leg elastic member 58 has a front terminal point 63 and a back terminal point 65, which represent the longitudinal ends of the elastic gathering caused by the leg elastic members. For clarity, the pants 20 have been illustrated in FIGS. 2 and 3 without gathering. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del., U.S.A.

The outer cover 40 desirably comprises a material which is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which the liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumberg, Ill., U.S.A.

If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 1 and 2, the training pants 20 and in particular the outer cover 40 may include one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product. However, appearance-related components may be omitted in the context of the present invention.

The illustrated pair of training pants 20 is designed for use by young girls and includes a registered outer cover graphic 60 (FIG. 2). In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for a training pants intended for use by young girls, so as to be aesthetically and/or functionally pleasing to them and the caregiver. The appearance-related components are desirably positioned on the training pants 20 at selected locations, which can be carried out using the methods disclosed in U.S. Pat. No. 5,766,389 issued Jun. 16, 1998 to Brandon et al., the entire disclosure of which is incorporated herein by reference. The primary pictorial image 61 is desirably positioned in the front waist region 22 along the longitudinal center line of the training pants 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C., U.S.A. and Glucopan 220UP from Henkel Corporation of Ambler, Pa. in an active ratio of 3:1. The surfactant can be applied by any conventional means, such as spraying, printing, brush coating, or the like. The surfactant can be applied to the entire bodyside liner 42 or can be selectively applied to particular sections of the bodyside liner, such as the medial section along the longitudinal center line.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. The outer cover 40, bodyside liner 42 and other materials used to construct the pants can comprise elastomeric or nonelastomeric materials.

The absorbent assembly 44 (FIG. 3) is positioned between the outer cover 40 and the bodyside liner 42, which can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes, and may be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 comprises a blend of wood pulp fluff and superabsorbent material. One preferred type of pulp is identified with the trade designation CR1654, available from U.S. Alliance, Childersburg, Ala., U.S.A., and is a bleached, highly absorbent sulfate wood pulp containing primarily soft wood fibers and about 16 percent hardwood fibers. As a general rule, the superabsorbent material is present in the absorbent assembly 44 in an amount of from 0 to about 90 percent weight based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent chassis 32 can also incorporate other materials designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C., U.S.A.

As noted previously, the illustrated training pants 20 have front and back side panels 34 and 134 disposed on each side of the absorbent chassis 32. The front side panels 34 can be permanently bonded along seams 66 to the composite structure 33 of the absorbent chassis 32 in the respective front and back waist regions 22 and 24. More particularly, as seen best in FIGS. 2 and 3, the front side panels 34 can be permanently bonded to and extend transversely outward beyond the side edges 47 of the composite structure 33 in the front waist region 22, and the back side panels 134 can be permanently bonded to and extend transversely outward beyond the side edges of the composite structure in the back waist region 24. The side panels 34 and 134 may be bonded to the composite structure 33 using attachment mechanisms known to those skilled in the art such as adhesive, thermal or ultrasonic bonding. Alternatively, the side panels 34 and 134 can be formed as an integral portion of a component of the composite structure 33. For example, the side panels can comprise a generally wider portion of the outer cover 40, the bodyside liner 42, and/or another component of the absorbent chassis 32. The front and back side panels 34 and 134 can be permanently bonded together or be releasably engaged with one another as illustrated by the fastening system 80.

The illustrated side panels 34 and 134 each have an outer edge 68 spaced laterally from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the composite structure 33 to the outer edges 68. The leg end edges 70 of the side panels 34 and 134 form part of the side edges 36 of the absorbent chassis 32. In the back waist region 24, the leg end edges 70 are desirably although not necessarily curved and/or angled relative to the transverse axis 49 to provide greater coverage toward the back of the pants 20 as compared to the front of the pants. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis.

In particular embodiments for improved fit and appearance, the side panels 34, 134 desirably have an average length measured parallel to the longitudinal axis 48 which is about 15 percent or greater, and particularly about 25 percent or greater, of the overall length of the pants, also measured parallel to the longitudinal axis 48. For example, in training pants 20 having an overall length of about 54 centimeters, the side panels 34, 134 desirably have an average length of about 10 centimeters or greater, such as about 15 centimeters. While each of the side panels 34, 134 extends from the waist opening 50 to one of the leg openings 52, the illustrated back side panels 134 have a continually decreasing length dimension moving from the attachment line 66 to the outer edge 68, as is best shown in FIGS. 2 and 3.

Each of the side panels 34 and 134 can include one or more individual, distinct pieces of material. In particular embodiments, for example, each side panel 34, 134 can include first and second side panel portions that are joined at a seam, or can include a single piece of material which is folded over upon itself (not shown).

The side panels 34, 134 desirably although not necessarily comprise an elastic material capable of stretching in a direction generally parallel to the transverse axis 49 of the training pants 20. Suitable elastic materials, as well as one process of incorporating elastic side panels into training pants, are described in the following U.S. Patents: U.S. Pat. Nos. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The illustrated training pants 20 includes the fastening system 80 for refastenably securing the training pants about the waist of the wearer. The illustrated fastening system 80 includes fastening components 82 adapted for refastenable engagement to corresponding second fastening components 84. In one embodiment, one surface of each of the first fastening components 82 comprises a plurality of engaging elements which project from that surface. The engaging elements of the first fastening components 82 are adapted to repeatedly engage and disengage engaging elements of the second fastening components 84.

The fastening components can comprise separate elements bonded to the side panels, or they may be integrally formed with the side panels. Thus, unless otherwise specified, the term "fastening component" includes separate components which function as fasteners, and regions of materials such as the side panels which function as fasteners. Moreover, a single material can define multiple fastening components to the extent that different regions of the material function as separate fasteners. The fastening components 82, 84 can be located on the side panels, between the side panels such as on the absorbent chassis, or a combination of the two. In the illustrated embodiment, the second fastening component 84 comprises a region of each rear side panel 134. The rear side panels 134 are made of loop material and the first fastening components 82 of hook material are applied to the front side panels 34. The "region" corresponding to the second fastening component 84 can be coextensive with the entire inner surface of each rear side panel 134, as is the case in the illustrated embodiment. Generally, the region of the inner surface which engages the first fastening component 82 when the fastening components are engaged is considered the second fastening component 84. Thus, the illustrated embodiment shows a combination of a fastening component which is separate from the front side panel 34 (the first fastening component 82) and a fastening component which is part of the rear side panel 134 (second fastening component 84).

The fastening components 82, 84 can comprise any refastenable fasteners suitable for absorbent articles, such as adhesive fasteners, cohesive fasteners, mechanical fasteners, or the like. In particular embodiments the fastening components comprise mechanical fastening elements for improved performance.-Suitable mechanical fastening elements can be provided by interlocking geometric shaped materials, such as hooks, loops, bulbs, mushrooms, arrowheads, balls on stems, male and female mating components, buckles, snaps, or the like.

A refastenable fastening system 80 allows for easy inspection of the interior of the pant-like product. If necessary, the fastening system 80 also allows the pant 20 to be removed quickly and easily. This is particularly beneficial when the pant contains messy excrement. For training pants 20, the caregiver can completely remove the pant-like product and replace it with a new one without having to remove the child's shoes and clothing.

As previously stated, in the illustrated embodiment the first fastening components 82 comprise hook fasteners and the second fastening components 84 comprise complementary loop fasteners. In another particular embodiment, the first fastening components 82 comprise loop fasteners and the second fastening components 84 comprise complementary hook fasteners. Although the training pants 20 illustrated in FIG. 1 show the back side panels 134 overlapping the front side panels 34, which is convenient, the training pants 20 can also be configured so that the front side panels overlap the back side panels. One skilled in the art will recognize that the shape, density and polymer composition of the hooks and loops may be selected to obtain the desired level of engagement between the fastening components 82, 84. A more aggressive hook material may comprise a material with a greater average hook height, a greater percentage of directionally-aligned hooks, or a more aggressive hook shape.

Loop fasteners typically comprise a fabric or nonwoven material having a plurality of loop members extending upwardly from at least one surface of the material. The loop material can be formed of any suitable woven or nonwoven material, such as acrylic, polyamide, polyethylene, polypropylene or polyester, and can be formed by methods such as warp knitting, stitch bonding or needle punching. Loop materials can also comprise any fibrous structure capable of entangling or catching hook materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in U.S. Pat. No. 5,858,515 issued Jan. 12, 1999 to Stokes et al.

Hook fasteners typically comprise a fabric or material having a base or backing structure and a plurality of hook members extending upwardly from at least one surface of the backing structure. In contrast to the loop fasteners which desirably comprise a flexible fabric, the hook material advantageously comprises a resilient material to minimize unintentional disengagement of the fastening components as a result of the hook material becoming deformed and catching on clothing or other items. The term "resilient" as used herein refers to an interlocking material having a predetermined shape and the property of the interlocking material to resume the predetermined shape after being engaged with and disengaged from a mating, complementary interlocking material. Suitable hook material can be molded or extruded from polyamide, polyethylene, polypropylene or another suitable material. Suitable single-sided hook materials for the fastening components 82, 84 are available from commercial vendors such as Velcro Industries B.V., Amsterdam, Netherlands or affiliates thereof, and are identified as Velcro HTH-829 with a uni-directional hook pattern and having a thickness of about 0.9 millimeters (35 mils) and HTH-851 with a uni-directional hook pattern and having a thickness of about 0.5 millimeters (20 mils); and Minnesota Mining & Manufacturing Co., St. Paul, Minn. U.S.A., including specific materials identified as CS-600.

With particular reference to FIG. 2, the first fastening components 82 are disposed on the outer surface 30 of the front side panels 34. The first fastening components 82 are desirably positioned along the outer edges 68 of the front side panels 34, abutting or adjacent to the waist end edge 72. As an example, the first fastening components 82 can be spaced inward from the outer edges 68 of the front side panels 34, in the range of about 0 to about 25 mm. It is understood that fastening components (not shown) may also extend laterally out beyond the outer edges 68 of the side panels 34, 134.

The training pants 20 can include an integral second fastening material (not shown) disposed in the front waist region 22 for refastenably connecting to the second fastening components 84 at two or more different regions, which define the first fastening components 84. In a particular embodiment, the fastening components 82, 84 can comprise integral portions of the waist regions 22, 24. For instance, one of the elastomeric front or back side panels 34, 134 can function as one of the fastening components (82 or 84) in that they can comprise a material which is releasably engageable with the other fastening components (84 or 82) disposed in the opposite waist region.

The first fastening components 82 of the illustrated embodiments are rectangular, although they may alternatively be square, round, oval, curved or otherwise non-rectangularly shaped. In particular embodiments, each of the fastening components 82 extends lengthwise generally parallel to the longitudinal axis 48 of the training pants 20 and extends widthwise generally parallel to the transverse axis 49 of the training pants. For a child of about 9 to about 15 kilograms (20–30 pounds), for example, the length of the first fastening components 82 is desirably from about 5 to about 13 centimeters, such as about 10 centimeters, and the width is desirably from about 0.5 to about 3 centimeters, such as about 1 centimeter. With particular embodiments, the first fastening components 82 have a length-to-width ratio of about 2 or greater, such as about 2 to about 25, and more particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

As shown in FIG. 1, when the fastening components 82, 84 are releasably engaged, the side edges 36 of the absorbent chassis 32 in the crotch region 26 define the leg openings 52, and the waist edges 38 and 39 of the absorbent chassis, including the waist end edges 72 of the side panels 34, 134, define the waist opening 50. For improved formation of the leg openings 52, it can be desirable in some embodiments for the front side panels 34 to be longitudinally spaced from the back side panels 134 as shown in FIGS. 2 and 3. For example, the front side panels 34 can be longitudinally spaced from the back side panels 134 by a distance equal to about 20 percent or greater, particularly from about 20 to about 75 percent, and more particularly from about 35 to about 50 percent, of the overall length of the pants 20.

When engaged, the fastening components 82, 84 define refastenable engagement seams 88 (FIG. 1) that desirably although not necessarily extend substantially the entire distance between the waist opening 50 and the leg openings 52. More specifically, the engagement seams 88 can cover about 75 to 100 percent, and particularly about 90 to about 98 percent, of the distance between the waist opening 50 and each leg opening 52, which distance is measured parallel to the longitudinal axis 48. To construct the engagement seams 88 to extend substantially the entire distance between the waist and leg openings 50 and 52, the first fastening components 82 can be formed to cover about 75 to 100 percent, and more particularly about 90 to about 98 percent, of the distance between the waist end edge 70 and the leg end edge 72 of the front side panels 34. In other embodiments (not shown), the fastening components can comprise a plurality of smaller fastening elements covering a smaller portion of the distance between the waist opening 50 and the leg openings 52, for example, about 20 to about 75 percent, but spaced apart to span a larger percentage of the distance covered by the smaller fastening elements between the waist opening and the leg openings.

Figure 4:
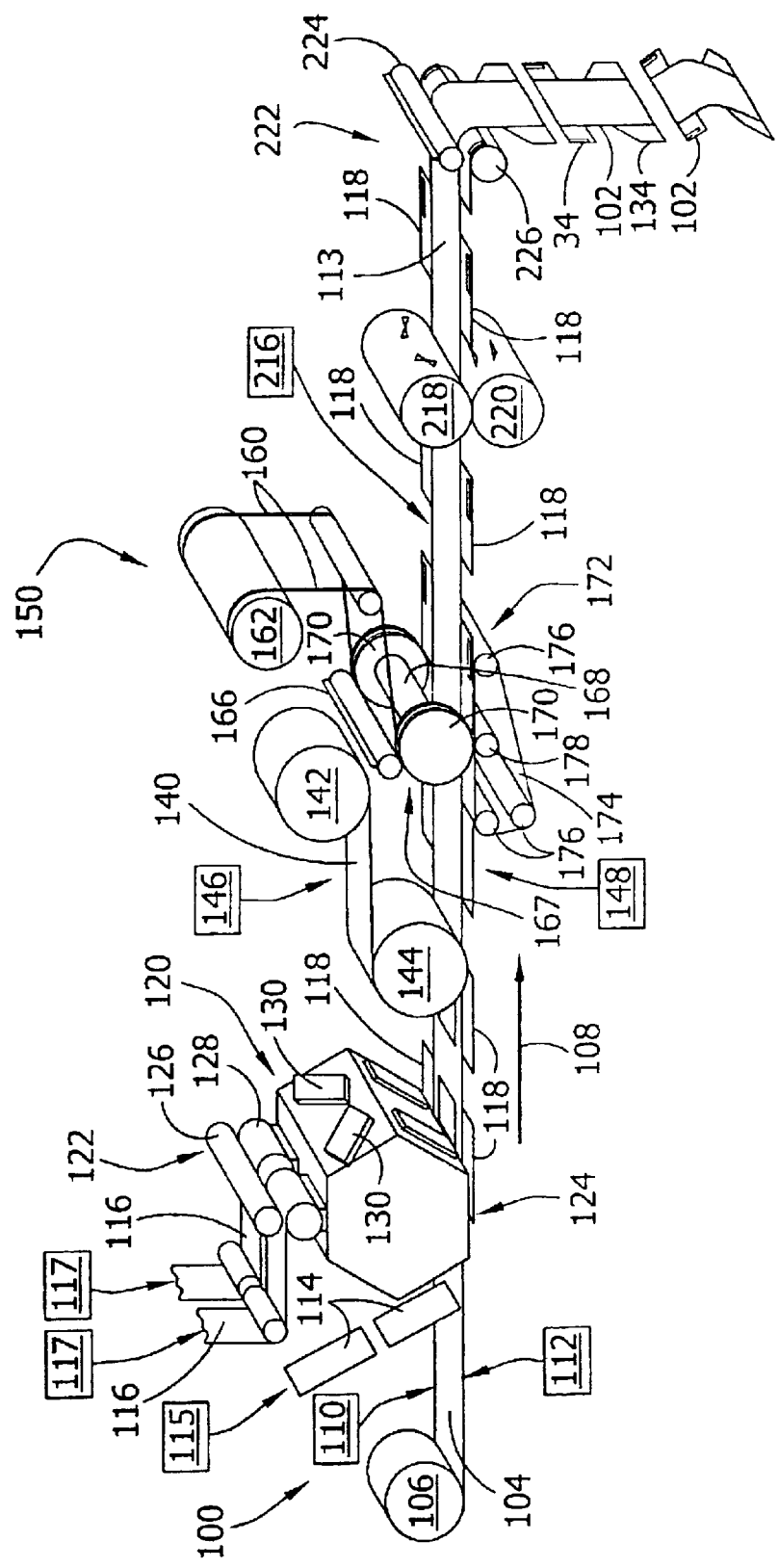
FIG. 4 is a schematic of an assembly section of apparatus for making garments such as training pants.

FIG. 4 generally illustrates apparatus of the present invention for use in making a pre-fastened garment, and more particularly for partially forming the training pants 20 and applying one of the first fastening components 82 to the training pants. Other arrangements of fastening components, described previously, may be used without departing from the scope of the present invention. Generally, the present invention has particular application for applying to the side panels 34, 134 one or two fastening components which are separate from the side panels. However, the principles of the present invention extend beyond the assembly of fastening components to partially assembled training pants 102, and beyond the assembly of training pants or other absorbent articles. The various components of the training pants 20 can be connected together by any means known to those skilled in the art such as, for example, adhesive, thermal and/or ultrasonic bonds. Desirably, most of the components are connected using ultrasonic bonding for improved manufacturing efficiency and reduced raw material costs. Certain garment manufacturing equipment which is readily known and understood in the art, including frames and mounting structures, ultrasonic and adhesive bonding devices, transport conveyors, transfer rolls, guide rolls, tension rolls, and the like, have not been shown in FIG. 4. Suitable absorbent supply mechanisms, web unwinds, conveyor systems, registration systems, drive systems, control systems and the like, for use with the present apparatus are disclosed in U.S. Pat. No. 5,766,389 issued Jun. 16, 1998 to Brandon et al., the entire disclosure of which is incorporated herein by reference. Also, the outer cover graphics 61 are not shown in FIG. 4.

A continuous web 104 of material used to form the bodyside liner 42 is provided from a supply source 106. The supply source 106 can comprise for example any standard unwind mechanism, which generally includes a pair of spindles, a festoon assembly, and a dancer roll for providing bodyside liner web 104 at a desired speed and tension. The spindles, festoon assembly and dancer roll are not illustrated in FIG. 4.

Various components can be disposed on and/or bonded to the bodyside liner web 104 as the web travels in a machine direction identified by arrow 108 in an assembly section 100 of the apparatus. In particular, a surge layer (not shown) can be provided at an application station 110 and disposed on and/or bonded to the bodyside liner web 104. The surge layer can comprise either a continuous web or discrete sheets. Additionally, a containment flap module 112 can be provided downstream from the supply source 106 for attaching pre-assembled containment flaps to the bodyside liner web 104. As various components are added in the assembly section 100, a continuously moving product assemblage 113 is formed. The product assemblage 113 is cut to form the partially assembled, discrete training pants 102.

A plurality of absorbent assemblies 114 can be provided from a suitable supply source 115. The supply source 115 can be any conventional mechanism for supplying the absorbent assemblies 114. Generally, a conventional supply source can include a hammermill for forming fluff fibers and, if desired, for providing an enclosure for mixing superabsorbent material with the fluff fibers, and then depositing the fluff and superabsorbent material on a forming drum having a desired absorbent design. The individual absorbent assemblies 114 can be disposed intermittently on the continuously moving bodyside liner web 104, one for each pair of training pants. The position of the absorbent assemblies 114 can be registered with the position of the surge material, if employed. The absorbent assemblies 114 can be bonded to one or more other components using adhesives or other suitable means. Alternatively, composite absorbent materials can be fed into the converting process from rolls or compressed packages, such as festooned bales.

Continuous webs of material 116 used to form the side panels 34, 134 can be provided from suitable supply sources 117. The supply sources can comprise one or more standard unwind mechanisms. The side panel material 116 can be cut into individual strips 118 and positioned partially on the bodyside liner web 104 using an applicator device 120. In the cross machine direction, the individual strips 118 desirably extend laterally outward from the bodyside liner web 104 and overlap the bodyside liner web by an amount such as about 2 or more centimeters to permit bonding of the strips to the bodyside liner and/or the containment flap material. In the machine direction 108, the position of the strips 118 can be registered relative to the absorbent assemblies 114 so that the product assemblage 113 can be cut between the absorbent assemblies with each strip 118 of side panel material 116 forming both a front side panel 34 and a back side panel 134 of consecutive pants 102. The strips 118 are later cut to form the separation of the side panels observed in FIGS. 2 and 3.

One suitable applicator device 120 is disclosed in U.S. Pat. No. 5,104,116 issued Apr. 14, 1992 and U.S. Pat. No. 5,224,405 issued Jul. 6, 1993 both to Pohjola, which are incorporated herein by reference. The applicator device 120 can comprise a cutting assembly 122 and a rotatable transfer roll 124. The cutting assembly 122 employs a rotatable knife roll 126 and a rotatable vacuum anvil roll 128 to cut individual strips 118 from the continuous side panel material 116. The strips 118 cut by a blade on the knife roll 126 can be maintained on the anvil roll 128 by vacuum and transferred to the transfer roll 124.

The rotatable transfer roll 124 can comprise a plurality of rotatable vacuum pucks 130. The vacuum pucks 130 receive the strips 118 of material 116 from the cutting assembly 122 and rotate and transfer the strips to the continuously moving bodyside liner web 104. When the strips 118 are positioned as desired relative to the bodyside liner web 104, the strips are released from the pucks 130 by extinguishing the vacuum in the pucks. The pucks 130 can continue to rotate toward the cutting assembly 122 to receive other strips. As disclosed by Van Gompel et al., the material 116 used to form the side panels can alternatively be provided in continuous form and pressurized fluid-jets or a rotary die cutter can be employed to cut the material to form leg openings 52. Still alternatively, the side panels 34, 134 of the training pants 20 can be provided by portions of the bodyside liner 42 and/or outer cover 40.

A continuous supply of material used to form the outer cover 40 extends in a web 140 from a supply roll 142 or other suitable source. The outer cover material 140 can be transported over a laminator roll 144 and bonded to the bodyside liner web 104. The absorbent assemblies 114 are thereby sandwiched between the continuous webs 104 and 140. The inward portions of the strips 118 of side panel material 116 can also be disposed between the bodyside liner web 104 and the outer cover web 140. Alternative configurations for attaching the side panel material 116 are disclosed by Van Gompel et al. Various components such as leg elastics 58 or waist elastics 54 and 56 can be bonded to the outer cover material web 140 at an application station 146 prior to uniting the bodyside liner and outer cover webs 104 and 140. Alternatively, leg elastics or waist elastics can be initially bonded to the bodyside liner web 104 or another material.

Bonding devices 148 such as ultrasonic bonders can be employed downstream from the laminator roll 144 to bond the bodyside liner web 104, side panel strips 118 and outer cover web 140. For example, these materials can be transported between a rotary ultrasonic horn and an anvil roll (not shown). Suitable rotary ultrasonic horns are described in U.S. Pat. No. 5,110,403 to Ehlert, which is incorporated herein by reference. Such rotary ultrasonic horns generally have a diameter of from about 5 to about 20 centimeters and a width of from about 2 to about 15 centimeters. Alternatively, the ultrasonic horn may be a stationary ultrasonic horn as is also known to those skilled in the art. Other suitable ultrasonic horns and ultrasonic bonders are commercially available from Branson Sonic Power Company, Danbury, Conn., U.S.A. The bonding devices 148 could otherwise be a thermal or adhesive bonder, as are well known. Adhesive could be used instead of or in conjunction with ultrasonic bonding.

The continuously moving product assemblage 113 next advances to a fastener application station 150 where first fastening components 82 are formed and bonded to the strips 118 of side panel material 116. As shown in FIG. 4, the product assemblage 113 is arranged so that the upward facing surface of the assemblage will become the outer surface 30 of the training pants 20 and the downward facing surface will become the inner surface 28. However, it is understood that the apparatus could alternatively employ any combination of different orientations. For example, the upward facing surface of the product assemblage 113 could form the inner surface 28 of finished garments. The front waist 22 of a leading garment is connected to the back waist region 24 of the trailing garment, but the back waist of a leading garment can be connected to the front waist of a trailing garment, or the garments can be arranged in a front-to-front/back-to-back relationship. Still alternatively, the apparatus could be constructed as a cross-machine direction process wherein the longitudinal axis 48 of each garment could be perpendicular to the machine direction 108 during part or all of the assembly process.

With reference again to FIG. 4, two continuous webs 160 of a first fastener material used to form the first fastening components 82 extend from supply rolls 162, which may form part of a first fastener material feeder. In the illustrated embodiment, the first fastener material is hook material, but may be loop material or other fastening material. The storage and delivery of the webs 160 to be cut into fastening components 82 may be other than described without departing from the scope of the present invention. The first fastener material webs 160 each are cut into individual first fastening components 82 by a knife roll 166 acting against an anvil roll 167. The continuous first fastener materials 160 are cut by a blade on the knife roll 166, maintained on the anvil roll 167 by vacuum, and adhered on the top surfaces of the strips 118 of side panel material 116, as will be described in more detail hereinafter. The anvil roll 167 includes a shaft 168 and wheels 170 mounted on the shaft for conjoint rotation therewith in a counterclockwise direction as viewed in FIGS. 4–8.

Figure 5:
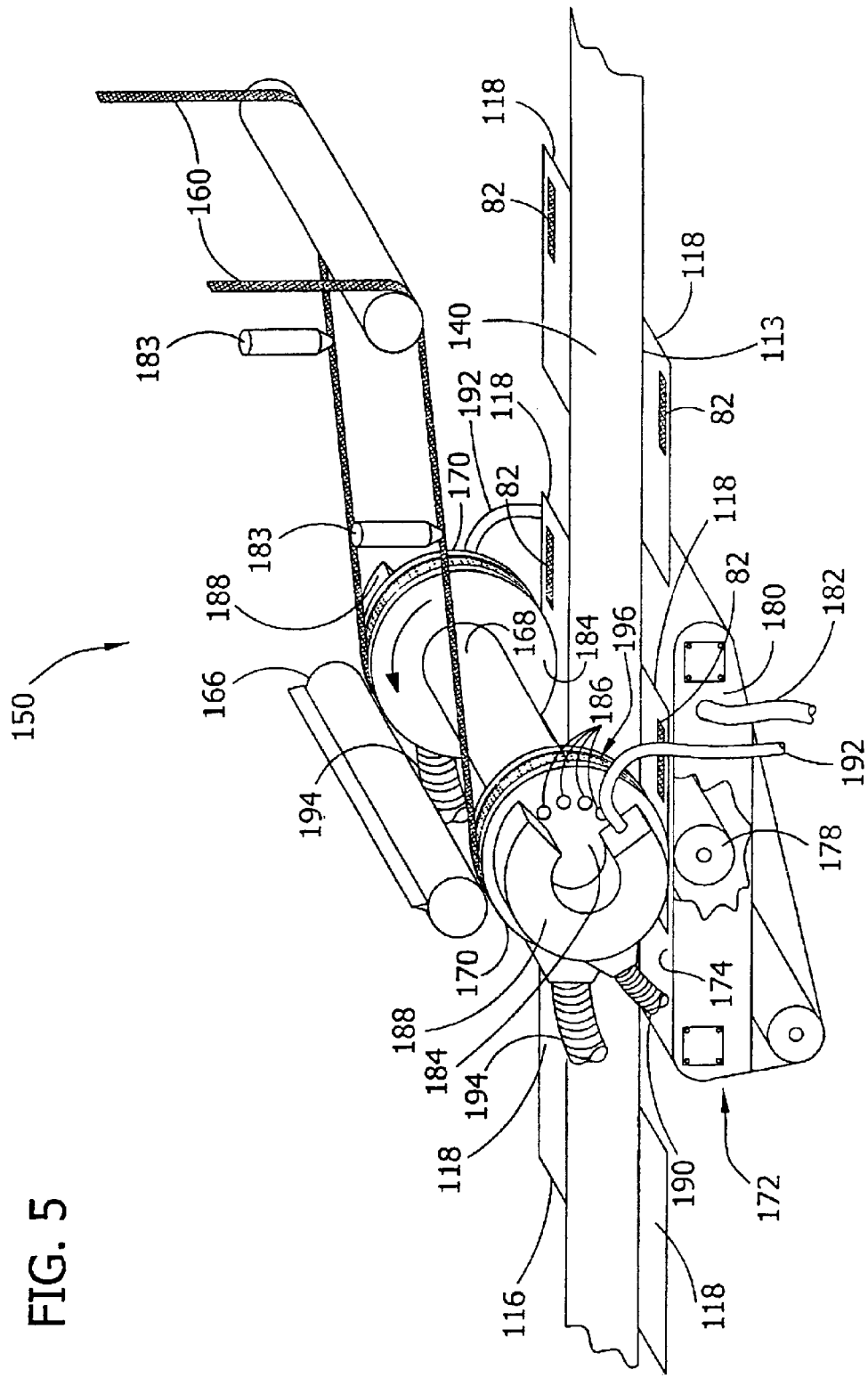
FIG. 5 is a schematic perspective of a fastener application station of the apparatus.

In order to accurately position the strips 118 of side panel material 116 for placement of the fastening components 82 thereon, a vacuum conveyor, indicated generally at 172, is positioned underneath the assemblage 113 partially opposite both wheels 170. The conveyor 172 includes an air permeable endless belt 174 (broadly, "a movable support") mounted around rollers 176, and a press (or "reaction") roll 178 located under the belt directly opposite each of the wheels 170. The term "movable support" as used herein broadly refers to movement of the support past the wheel 170 for receiving a fastening component 82, although other movements are not excluded. As shown in FIG. 5, part of the interior of the conveyor 172 is closed off by walls 180 (only one of which is shown) so that a vacuum may be drawn in the interior. The wall 180 shown in FIG. 5 has been broken away to show the press roll 178. The interior of the conveyor 172 is connected by a conduit 182 to a vacuum source (not shown). The construction of the vacuum conveyor 172 may be other than specifically described without departing form the scope of the present invention. For example, the vacuum conveyor may include more than one belt conveyor, one or more drums or rollers or some combination of these conveyors without departing from the scope of the present invention. The permeable belt 174 communicates the vacuum pressure to the strips 118 lying on an upper reach of the conveyor belt, securely holding the strips flat against the belt. Straightening devices can be used to straighten the strips 118 before or while being placed on the conveyor 172. For example, nozzles (not shown) may be provided to blow air over the strips in a direction tending to straighten out the strips and cause them to lie flat. The vacuum conveyor 172 also helps to locate the assemblage 113 laterally of the conveyor so that the strips 118 are in the proper position for receiving the fastening components 82. The knife roll 166, anvil roll 167 and conveyor 172 are driven by way of a take off from an assembly line drive shaft (not shown). In this way synchronized operation of the fastener application station 150 can be achieved. Suitable gearing (not shown) can be employed to achieve the exact rotation/travel rates of the knife roll 166, anvil roll 167 and conveyor 172.

However, it is to be understood that other ways of driving the components of the fastener application station 150 may be used without departing from the scope of the present invention.

Referring to FIG. 5, the webs 160 of hook material pass from the supply rolls 162 past adhesive applicators 183 which apply adhesive to the back (upwardly facing) side of the webs. Each web 160 extends onto a respective one of the wheels 170 of the anvil roll 167. The wheels 170 each have spaced apart side walls 184. The laterally outer side walls 184 of each wheel 170 have holes 186 arranged in angularly spaced positions along a circle. The holes 186 extend inwardly across the wheel 170, and are closed at the opposite side of the wheel. As described in more detail hereinafter, the interior of each hole is capable of communicating with a circumferential ("exterior") surface of the wheel 170 for applying a vacuum or positive air pressure to the circumferential surface. A generally C-shaped pressure shoe 188 is mounted in fixed position next to the laterally outer side wall 184 of each wheel 170. Each shoe 188 is closed on its inner side only by the laterally outer side wall 184, and has a sliding, sealing engagement with the side wall to prevent air from leaking into or out of the shoe between the shoe and side wall, while permitting the side wall to slide past the shoe as the wheel 170 rotates. As the holes 186 pass under the shoe 188, they communicate the positive or negative air pressure to the circumferential surface of the wheel 170. The interior of the shoe 188 is compartmentalized so that portions of the shoe are subject to differing levels of vacuum pressure supplied by way of a conduit 190 (the conduit of only one of the shoes being illustrated in the drawings). A compartment (not shown) at the bottom of the wheel 170 can be subject to positive air pressure supplied by a conduit 192, which effectively negates or neutralizes the vacuum. Rejection chutes 194 provided adjacent upstream sides of respective wheels 170 remove fastening components 82 from the wheels in case of a problem with movement of the assemblage 113. The chutes 194 are connected to a vacuum source (not shown) capable of being selectively activated, such as upon detection of a problem with movement of the assemblage 113, to capture fastening components 82 from the wheel 170 and prevent the conveyor belt 174 from becoming fouled with adhesive.

Figure 13:
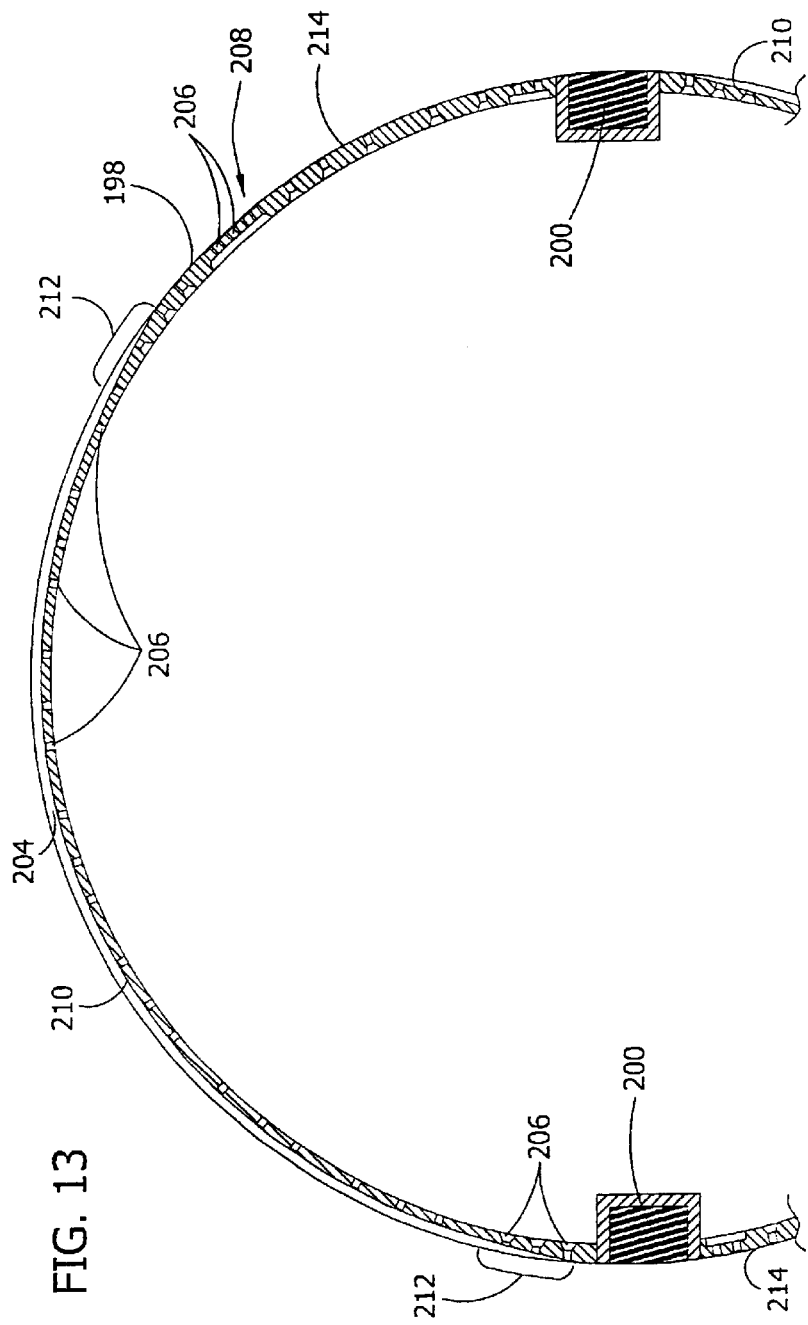
FIG. 13 is a fragmentary section of the shell as it would be mounted on the anvil roll.

The wheels 170 of the anvil roll 167 are constructed to facilitate accurate placement of the fastening components 82 cut from the webs 160 of hook material. The construction of the wheels 170 is substantially identical in the illustrated embodiment, so only one of the wheels will be described. More particularly, the wheel 170 includes a shell (generally indicated at 196) which is mounted on the side walls 184 of the wheel and defines the circumferential surface which engages the web 160 and holds the fastening components 82 after they are severed from the web. FIG. 9 illustrates about one half of the shell 196 laid flat, while FIG. 13 shows a fragmentary section of the shell as it would be disposed on the wheel. The shell 196 includes two elongate plate sections 198 separated by anvil sections 200 (broadly, "inserts") which are periodically engaged by the blade of the knife roll 166 in operation. The plate sections 198 each include lateral portions 202 and a central channel 204 which engages the web 160 and fastening components 82. Groups of three holes 206 are arranged along the length of the plate section at unequal spacings. One cluster 208 of five groups of holes 206 is in each half of the shell 196. The clusters 208 concentrate the vacuum pressure in regions of the wheel 170 where the fastening components 82 reside after being cut from the web 160 for securely holding the fastening component 82 on the wheel. Elsewhere, the groups of holes 206 are spaced farther apart to facilitate slippage of the web 160 on the surface of the wheel 170. The number of holes 206 in a group and the spacing of the groups may be other than described without departing from the scope of the present invention. The holes 206 are flared outwardly near the outer surface of the plate section 198 (see FIGS. 10–12). The plate section is also undercut beneath the holes 206 to minimize their length and avoid clogging. In one embodiment, all of the compartments of the shoe 188 can be supplied with positive air pressure upon start up and/or shut down to blow out any debris in the holes 206. It is to be understood that the holes 206 may be formed by a screen (not shown) on the wheel 170, or in other suitable ways.

The central channels 204 of the plate sections 198 have depths which change along their lengths. More particularly, each channel has a groove indicated by reference numeral 210 in FIG. 13 which has tapering depth regions 212 near its ends. The groove 210 is located generally midway between the side walls 184 of the wheel 170 and has a width equal to that of the channel 204, although the groove may be otherwise positioned and have a width not co-extensive with the width of the channel. The tapering depth region 212 near the left end of the plate section 198 (as viewed in FIG. 13) is close to the anvil section 200 at the left end of the plate section. The depth of the channel 204 does not go to zero outside the groove, but is so shallow as to not be discernable on the scale of FIG. 13. The tapering depth region 212 of the groove 210 located nearer to the right end (as viewed in FIG. 13) of the plate section 198 is spaced well to the left of the anvil section 200 located on the right end of the plate section. The depth of the majority (and deepest part) of the groove 210 is illustrated in FIG. 10, and in one embodiment can be 0.125 inches (3.18 mm). The reduced depth of the groove 210 roughly midway along the tapering depth region 212 is shown in FIG. 11. Near the right and left ends of the plate section 198, outside the groove 210, the depth of the channel 204 is diminished to a very small amount (FIG. 12), for example about 0.008–0.009 inches (0.20–0.23 mm). The depths at the various locations may be other than described, and moreover, the depth of the channel 204 outside the groove may go to zero. Still further, the groove 210 may continue uninterrupted around the entire circumference of the wheel 170. The longer segment of the channel 204 outside the groove 210 near the right end of the plate section 198 defines a land 214 which is generally flush with the outer surface of the wheel 170 to facilitate release of a fastening component 82 onto a strip 118, as will be described.

Figure 6:
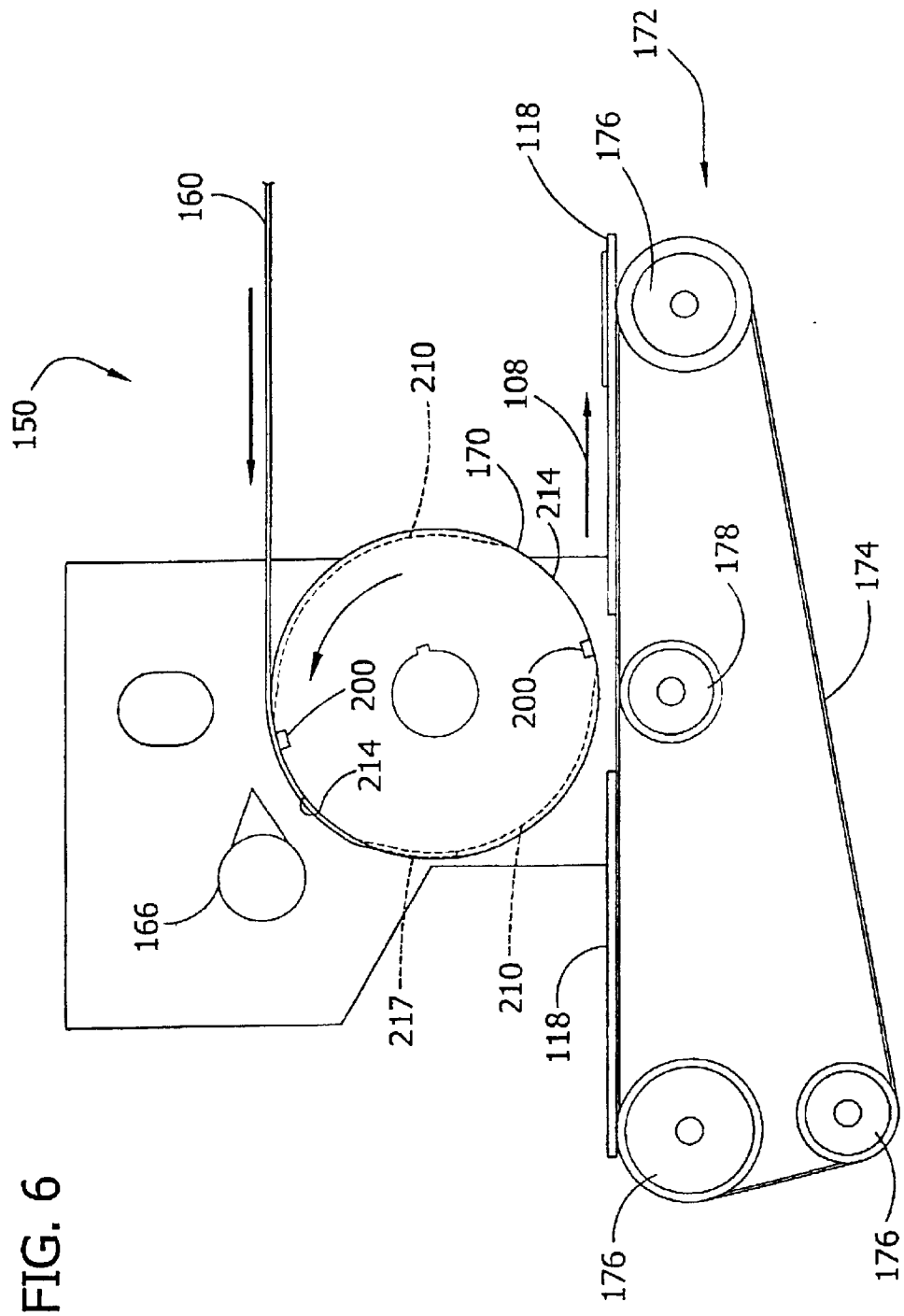
FIGS. 6–8 are diagrammatic elevations of the fastener application station illustrating its operation.
Figure 7:
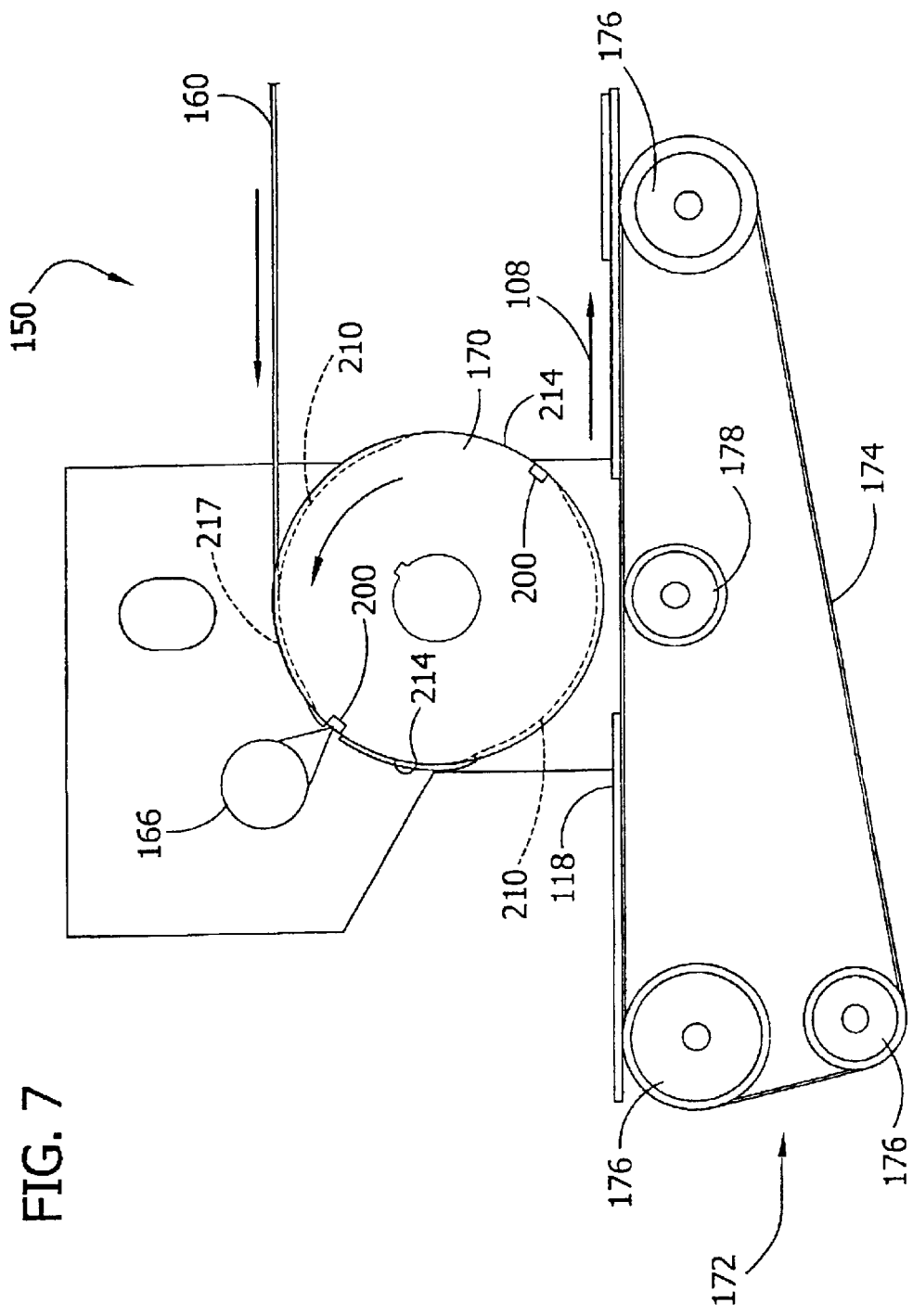
Figure 8:
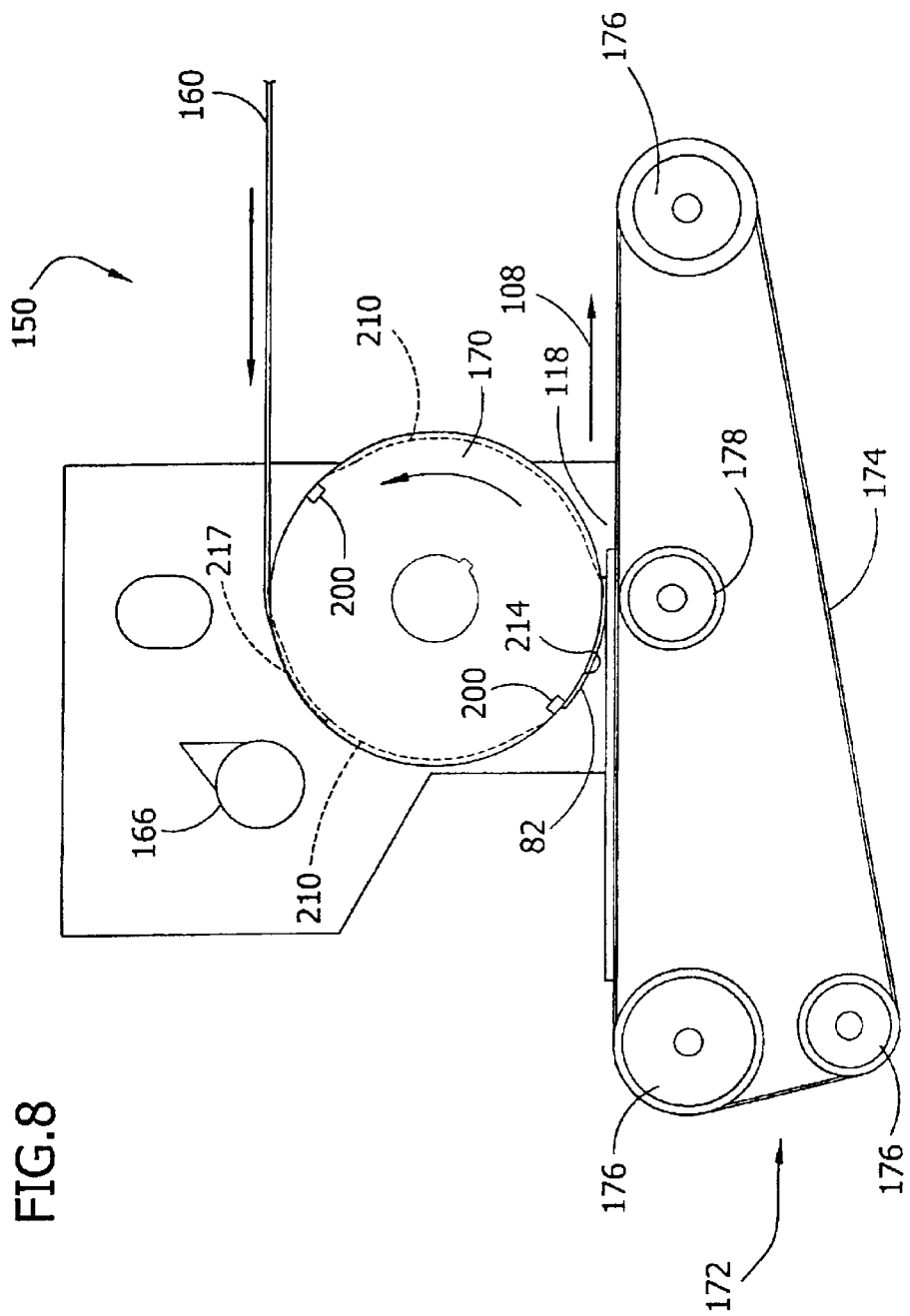

Having described the construction of the fastener application station 150, its operation will now be described with particular reference being made to FIGS. 6–8 of the drawings. The drawings illustrate the operation of one wheel 170, the operation of the other being substantially the same in the embodiment shown. The wheel 170 rotates in the direction indicated by the arrow in the figures at a constant speed. More particularly, the wheel 170 is made to rotate so that its velocity at the outer surface is the same as the velocity of the conveyor belt 174. The wheel 170 is sized so that one fastening component 82 is applied to one strip 118 of side panel material 116 for each half revolution of the wheel. The knife roll 166 is timed so that it turns twice for each revolution of the wheel 170, cutting two fastening components 82 from the web 160 of hook material in that time. It will be appreciated that the blade of the knife roll 166 will engage the anvil sections 200 of the wheel 170.

The web 160 of hook material is fed out at a rate which is slower (e.g., about one quarter) the speed of the wheel 170 in the direction indicated by the arrow above the web. Thus, the outer surface of the wheel 170 slides under the web 160. The vacuum applied through the holes 208 of the plate section 198 holds an end segment of the web 160 against the wheel 170 while permitting relative movement. At least a portion 217 of the end segment of the web 160 is received in the groove 210. This condition may be observed in FIGS. 6–8. The depth of the groove 210 restrains the end segment of the web 160 from significant lateral movement relative to the wheel 170 so that the web remains precisely located prior to being cut. As the knife roll 166 and wheel 170 near the point of engagement, more and more of the free end of the web 160 slides out of the groove 210 onto the land 214 immediately adjacent to the anvil section 200. It may be seen that more of the end segment portion 217 of the web 160 is located in the groove 210 in FIG. 8 than in FIG. 6 where the knife roll 166 is closer to making its cut. FIG. 7 illustrates the knife roll 166 and wheel 170 just after the moment of initial engagement of the knife roll with the wheel, severing one fastening component 82 (broadly, "cut piece" and "first cut piece") from the web 160. The fastening component 82 is rapidly accelerated to the speed of the wheel 170 and lies entirely or almost entirely on the land 214 substantially flush with the remainder of the outer surface of the wheel.

The fastening component 82 travels with the wheel 170 to the bottom of the wheel where it is applied to the strip 118 of side panel material 116 (broadly, "second cut piece") on the partially assembled training pants 102. In the illustrated embodiment, the other wheel 170 operates to apply another fastening component ("third cut piece") to another strip ("fourth cut piece") of side panel material. As stated above, the vacuum applied to the fastening component 82 by the wheel 170 is greatly reduced or eliminated near the bottom of the wheel. It is also envisioned that positive air pressure could be applied to blow the fastening component 82 off of the wheel onto the strip 118. A gap between the wheel 170 and the conveyor belt 174 which is larger than the thicknesses of the materials (e.g., the combined thickness of the fastening component 82, strip 118 and any adhesive or other fastening medium layer) could more readily be employed when positive air blow off is used on the anvil roll 167. In that event, the air blast will blow the strip 118 off of the anvil roll wheel 170, across the gap and onto to the side panel material 116 on the conveyor belt 174. When using an air blast, a nip roll or ironing roll (not shown) may be used downstream from the anvil roll 167 to press the strip 118 onto the side panel 116. Whether or not positive air pressure or a larger gap is used, the fastening component 82 and strip 118 could be pressed together at a station downstream of the anvil roll 167 if pressing was necessary to assure connection of the fastening component and strip.

Returning to the illustrated embodiment, the back side of the fastening component 82, to which adhesive was previously applied, engages the strip 118 and adheres to it. Moreover, the fastening component 82 may experience the vacuum of the vacuum conveyor 172 at this position, further promoting transfer of the fastening component from the wheel 170 to the strip 118. The spacing between the bottom of the wheel 170 and the top of the conveyor belt 174 at the point of transfer is less than or equal to the combined thickness of the fastening component 82, strip 118 and any adhesive or other fastening medium layer so that the wheel firmly presses the fastening component against the strip. The fastening component 82 is thus firmly pressed into the strip 118 at the transfer point. The spacing of the wheel 170 and conveyor belt 174 is selected so that it is not greater than the uncompressed assembly of elements received at the transfer point (or nip), whatever the exact composition of the assembly. In other words, the assembly may be just the fastening component 82 and the strip 118, these elements plus an adhesive layer, and/or an underlying carrier web for the strips 118 which is removed before final assembly of the training pants 20, to give a few examples.

In the illustrated embodiment, the conveyor belt 174 constitutes a "receiving member", which with the wheel 170 defines a transfer nip where the fastening component 82 is transferred from the wheel to the strip 118. However the receiving member can be a stationary surface or some other moving member such as a roll or reciprocating plate without departing from the scope of the present invention. Further, the press roll 178 is located opposite the wheel 170 at the transfer nip, supporting the conveyor belt 174 and fixing the separation of the upper surface of the conveyor belt and the outer surface of the wheel 170 at the transfer nip. The exterior cylindrical surface of the press roll 178 constitutes a reaction surface in the illustrated embodiment. However, it is to be understood that the press roll 178 may be omitted without departing from the scope of the present invention. In that even the conveyor belt 174 might be arranged to engage the wheel 170 (or to cause the strip 118 to engage the wheel) until a strip pushes the conveyor belt away from the wheel as it is being transferred to the strip on the conveyor belt. In this way, the strip 118 of side panel material 116 can be held flat and straight while permitting the fastening component 82 to be firmly pressed against the strip at the transfer nip.

Referring again to FIG. 4, additional bonding of the fastening components 82 to the strips may be carried out by a suitable bonding device such as an ultrasonic bonder 216 just downstream from the fastening component application station 150. The strips 118 of side panel material 116 can be trimmed if desired, for example to provide angled and/or curved leg end edges 70 in the back waist region 24 (FIGS. 2 and 3). To this end, the assembly section 100 can include a die cutting roll 218 and a backing roll 220. In the illustrated embodiment, a portion of each strip 118 is trimmed from a trailing edge thereof in order to form the angled and/or curved leg end edges 70 in the back waist region 24.

The method and apparatus to this point provides a continuous web of interconnected and partially assembled training pants moving in the direction indicated by arrow 108. This continuously moving product assemblage 113 is passed through a cutter 222 which selectively cuts the web into discrete, partially assembled training pants 102. Such cutters 222 are generally known to those skilled in the art and can include, for example, the combination of a cutting roll 224 and an anvil roll 226 through which the web travels. The anvil roll 226 can include a hardened steel rotating roll while the cutting roll 224 can include one or more flexible hardened steel blades clamped onto another rotating roll. The pinching force between the blade on the cutting roll 224 and the anvil roll 226 creates the cut. The cutting roll 224 can have one or more blades depending upon the desired distance between the cuts. The cutter 222 can further be configured to provide a spacing between the individual cut pieces after they are cut. Such a spacing can be provided by transferring the cut pieces away from the cutter 222 at a higher speed than the speed at which the web is provided to the cutter. Additional and well known steps (not shown) may be performed to complete assembly of the training pants 20.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for cutting and placing fastening components on pairs of side panels located on opposite sides of an assemblage in the manufacture of absorbent garments, the pairs of side panels being spaced apart in a machine direction, the apparatus comprising:
    a vacuum conveyor comprising a continuous belt and rollers mounted for movement of the continuous belt in a circuit, the continuous belt being adapted to support the assemblage on an upper reach thereof, and to locate the side panels on the upper reach as the assemblage is moved by the conveyor belt, and a vacuum plenum located under an upper reach of the conveyor belt for supplying a vacuum pressure adjacent to the upper reach, the conveyor belt being porous for communicating a vacuum pressure through the belt to the side panels;
    an anvil roll including two wheels mounted in generally opposed relation with the conveyor belt to define transfer nips, the wheels being adapted for rotation about an axis of rotation, each wheel being adapted to receive an end segment of a respective web of fastening component material thereon;
    a cutter roll mounted for rotation about an axis generally parallel to the axis of rotation of the wheels, the cutter roll including a knife periodically engageable with the fastening component material end segment on each wheel when the end segment is on the wheel for severing the fastening components from the web of fastening component material;
    the wheels being adapted to retain the fastening components thereon and to carry the fastening components to the upper reach of the conveyor belt for placement of the fastening components onto respective side panels.

2. A method of applying fastening components to an assemblage in the manufacture of disposable pants, the method comprising:
    cutting side panels for the disposable pants from a web of side panel material;
    attaching the cut side panels to the assemblage at spaced apart locations along the length of the assemblage;
    controlling the orientation and configuration of the side panels on a conveyor transporting the assemblage including the attached side panels;
    cutting fastening components from a web of fastening component material on an anvil roll adjacent to the conveyor;
    transporting the cut fastening components on the anvil roll to a transfer point between the anvil roll and conveyor; and
    transferring the cut fastening components at the transfer point from the anvil roll to the side panels controlled by the conveyor.

3. Apparatus for cutting and placing first cut pieces of material onto second pieces of material, the apparatus comprising:
    a vacuum conveyor including a movable support adapted to support said second pieces of material and to hold said second pieces in place on the movable support as the second pieces are moved by said movable support;
    an anvil roll including a wheel mounted in generally opposed relation with the movable support of the vacuum conveyor to define a transfer nip, the wheel being adapted for rotation about an axis of rotation, the wheel being adapted to receive an end segment of a web of said first material thereon;
    a cutter roll mounted for rotation about an axis generally parallel to the axis of rotation of the wheel, the cutter roll including a knife periodically engageable with said first material web end segment when the end segment is on the wheel for severing the first cut pieces of material from the web of first material, the wheel being adapted to retain said first cut pieces thereon and to carry said first out pieces to the movable support of the vacuum conveyor for placement of said first cut pieces on said second pieces, the wheel and movable support of the conveyor are adapted to move at about the same rate of linear velocity; and
    a feeder for feeding the web of said first material to the wheel at a speed less than the speed of the wheel.

4. Apparatus as set forth in claim 3 wherein the wheel includes a generally cylindrical circumferential surface adapted for receiving the end segment of the web of the first material for sliding engagement with the circumferential surface, a groove formed in the circumferential surface adapted to receive the end segment to align the end segment axially of the wheel, and a land disposed for receiving said first cut pieces of material to hold said first cut pieces of material for transporting said first cut pieces of material to the second pieces of material on the movable support of the vacuum conveyor.

5. Apparatus as set forth in claim 4 wherein the groove extends lengthwise generally circumferentially of the circumferential surface.

6. Apparatus as set forth in claim 5 wherein the groove has a gradually decreasing depth toward at least one end thereof adjacent to the land.

7. Apparatus as set forth in claim 6 wherein the groove has gradually decreasing depth toward both ends of the groove.

8. Apparatus as set forth in claim 4 wherein the wheel is constructed to release said first cut pieces at the transfer nip.

9. Apparatus as set forth in claim 8 wherein the wheel is adapted for connection to a vacuum source for use in retaining the end segment of the web of the first material and the first cut pieces of material on the wheel, the wheel being adapted to release the vacuum from said first cut pieces at the transfer nip.

10. Apparatus for cutting and placing first cut pieces of material onto second pieces of material, the apparatus comprising:

a vacuum conveyor including a movable support adapted to support said second pieces of material and to hold said second pieces in place on the movable support as the second pieces are moved by said movable support;

an anvil roll including a wheel mounted in generally opposed relation with the movable support of the vacuum conveyor to define a transfer nip, the wheel being adapted for rotation about an axis of rotation, the wheel being adapted to receive an end segment of a web of said first material thereon;

a cutter roll mounted for rotation about an axis generally parallel to the axis of rotation of the wheel, the cutter roll including a knife periodically engageable with said first material web end segment when the end segment is on the wheel for severing the first cut pieces of material from the web of first material, the wheel being adapted to retain said first cut pieces thereon and to carry said first cut pieces to the movable support of the vacuum conveyor for placement of said first cut pieces on said second pieces; and an applicator for applying an adhesive to the web of said first material for use in attaching said first cut pieces of material to said second pieces of material.

11. Apparatus as set forth in claim 10 wherein the vacuum conveyor further comprises a reaction surface generally opposite the wheel, the movable support being adapted to extend between the reaction surface and the wheel.

12. Apparatus as set forth in claim 11 wherein the vacuum conveyor further comprises a reaction roll, the reaction surface being defined by a surface of the reaction roll.

13. Apparatus as set forth in claim 11 wherein the reaction surface holds the movable support within a distance from the wheel less than the sum of the uncompressed thickness of an assembly of material received in the transfer nip, the assembly including the first and second pieces of material.

14. Apparatus as set forth in claim 10 further comprising a cut and place device for cutting said second pieces of material from a web of second material and placing said second pieces on the vacuum conveyor.

15. Apparatus as set forth in claim 10 wherein the wheel is constructed to release said first cut pieces at the transfer nip.

16. Apparatus as set forth in claim 15 wherein the wheel is adapted for connection to a vacuum source for use in retaining the end segment of the web of the first material and the first cut pieces of material on the wheel, the wheel being adapted to release the vacuum from said first cut pieces at the transfer nip.

17. Apparatus as set forth in claim 10 wherein the movable support comprises a continuous conveyor belt having an upper reach on which said second pieces of material are supported.

18. Apparatus for cutting and placing first cut pieces of material onto second pieces of material, the apparatus comprising:

a vacuum conveyor including a movable support adapted to support said second pieces of material and to hold said second pieces in place on the movable support as the second pieces are moved by said movable support;

an anvil roll including a wheel mounted in generally opposed relation with the movable support of the vacuum conveyor to define a transfer nip, the wheel being adapted for rotation about an axis of rotation, the wheel being adapted to receive an end segment of a web of said first material thereon;

a cutter roll mounted for rotation about an axis generally parallel to the axis of rotation of the wheel, the cutter roll including a knife periodically engageable with said first material web end segment when the end segment is on the wheel for severing the first cut pieces of material from the web of first material, the wheel being adapted to retain said first cut pieces thereon and to carry said first cut pieces to the movable support of the vacuum conveyor for placement of said first cut pieces on said second pieces; and a second wheel mounted in generally opposed relation with the movable support of the vacuum conveyor to define a second transfer nip, the second wheel being adapted for rotation about an axis of rotation and to receive an end segment of a web of a third material thereon for applying third cut pieces of material to fourth pieces of material on the movable support.

19. Apparatus as set forth in claim 18 wherein the second anvil is disposed relative to the cutter roll such that the knife is periodically engageable with said third material web end segment when the end segment is on the second wheel for severing one of the third cut pieces of material from the web of third material.

20. A method of cutting and placing first cut pieces of material on second pieces of material in a continuous process, the method comprising cutting the second pieces from a web of second material, depositing the second pieces on a conveyor, restraining the second pieces in position on the conveyor, rotating an anvil roll at a first rate, feeding a web of first material to the anvil roll at a second rate slower than said first rate whereby the web of material slides on the anvil roll, cutting the first cut pieces from the web of first material engaging the anvil roll, transporting the first cut pieces on the anvil roll to a transfer point at the conveyor, and transferring the first cut pieces to the second pieces on the conveyor at the transfer point.

21. A method as set forth in claim 20 wherein the first rate of rotation of the anvil roll is approximately equal to the speed of the conveyor at the transfer point.

22. A method as set forth in claim 20 further comprising supporting the conveyor on a side thereof generally opposite the anvil roll to hold the spacing of the anvil roll and the conveyor at the transfer point to less than the sum of the uncompressed thickness of an assembly of material received in the transfer point, the assembly including the first cut piece and the second piece.

23. A method as set forth in claim 20 further comprising restraining the first cut pieces of material on the anvil roll from a location where they are cut from the web of first material to the transfer point.

24. A method as set forth in claim 23 wherein restraining the first cut pieces comprises applying a vacuum to the first cut pieces on the anvil roll.

25. A method as set forth in claim 20 further comprising positioning an end segment of the web of first material axially of the anvil roll prior to cutting the first cut pieces of material from the web of first material.

26. A method as set forth in claim 25 wherein positioning the end segment of the web of first material comprises receiving the end segment in a groove extending circumferentially of the anvil roll.

* * * * *